United States Patent [19]

Seibold et al.

[11] Patent Number: 5,264,680
[45] Date of Patent: Nov. 23, 1993

[54] MODULAR BALL HEAD REMOVER

[75] Inventors: Horst R. Seibold, Bellevue; Raymond P. Robinson, Seattle, both of Wash.

[73] Assignee: Virginia Mason Clinic, Seattle, Wash.

[21] Appl. No.: 738,452

[22] Filed: Jul. 31, 1991

[51] Int. Cl.$^5$ .................... H05B 3/02; A61B 17/00
[52] U.S. Cl. .................... 219/227; 219/221; 219/230; 606/100
[58] Field of Search .......... 219/221, 227, 230; 606/99, 89, 100; 623/18, 22, 23

[56] References Cited

U.S. PATENT DOCUMENTS

| | | | |
|---|---|---|---|
| 2,725,878 | 12/1955 | Reiter | 128/305 |
| 3,467,811 | 9/1969 | Consoletti | 219/277 |
| 3,818,514 | 6/1974 | Clark | 3/1 |
| 3,857,389 | 12/1974 | Amstutz | 128/93 E C |
| 3,892,648 | 7/1975 | Phillips et al. | 204/181 |
| 4,222,382 | 9/1980 | Antonsson et al. | 128/303 R |
| 4,317,986 | 3/1982 | Sullivan | 219/231 |
| 4,399,813 | 8/1982 | Barber | 128/92 E C |
| 4,459,985 | 7/1984 | McKay et al. | 128/303 R |
| 4,462,395 | 7/1984 | Johnson | 128/92 B |
| 4,686,971 | 8/1987 | Harris et al. | 128/92 VT |
| 4,865,609 | 9/1989 | Roche | 623/23 |
| 5,037,442 | 8/1991 | Wintermantel | 623/23 |

Primary Examiner—Bruce A. Reynolds
Assistant Examiner—Michael D. Switzer
Attorney, Agent, or Firm—Seed and Berry

[57] ABSTRACT

An apparatus and method for removing a modular ball head from a prosthesis stem by heat expanding the modular ball head and subjecting it to an impact force in a direction such that it is removed from the prosthesis stem. A housing receives the modular ball head therein while the prosthesis stem is still within a patient's femur. A heater within the housing heats the modular ball head. An impact hammer comprised of a mass slideably mounted on a rod is attached to the housing and has an anvil stop at one end. The housing is thermally insulated to retain heat while protecting an operator and the patient from burns. The heat generated is controlled as to amount and duration.

24 Claims, 5 Drawing Sheets

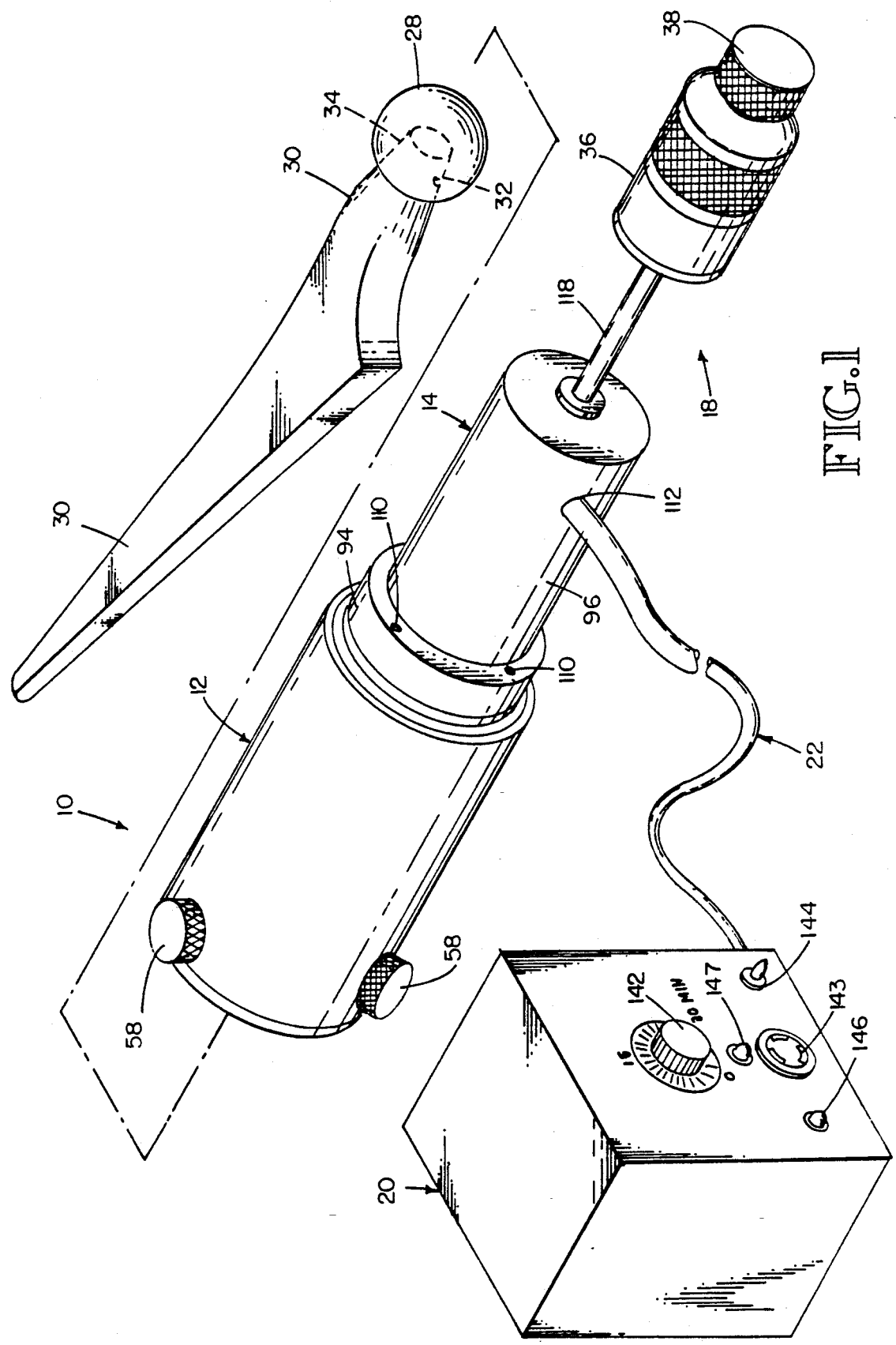

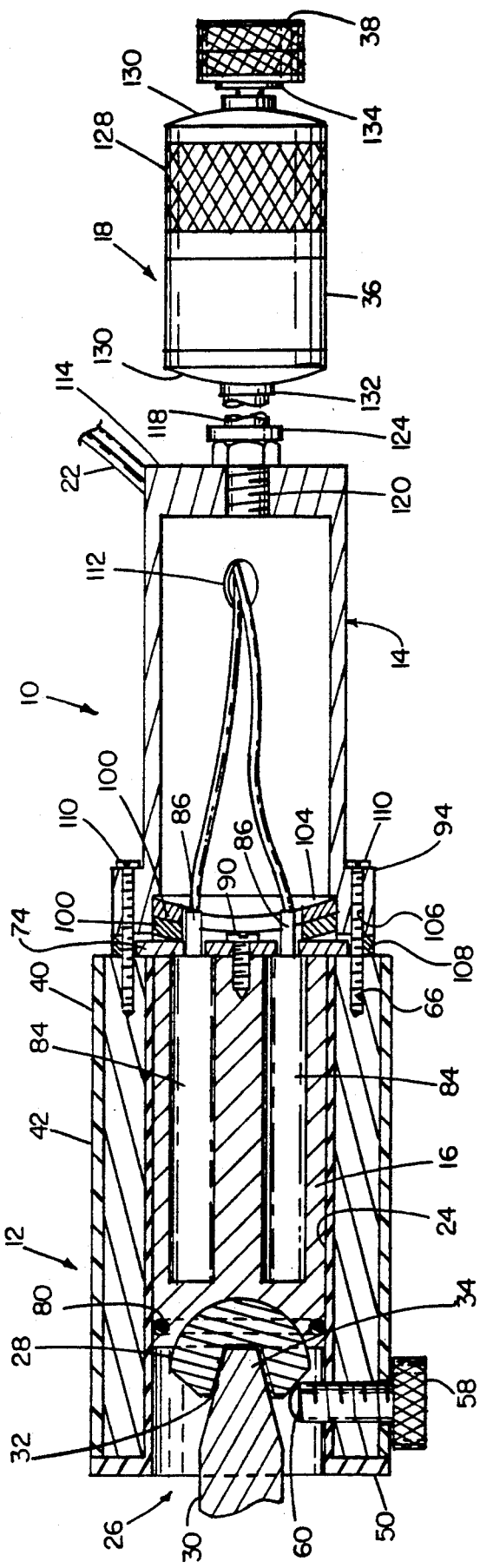

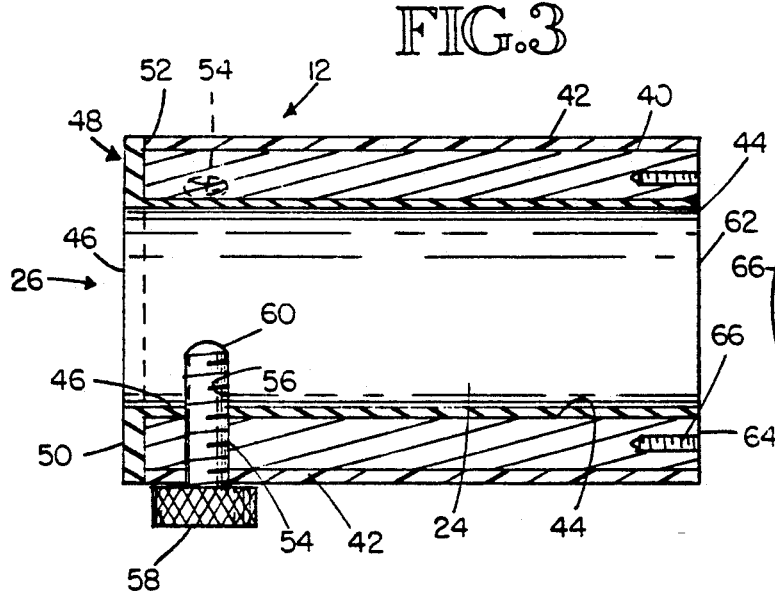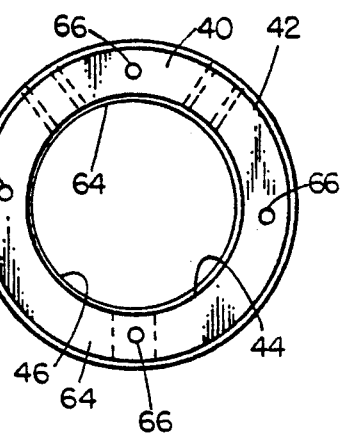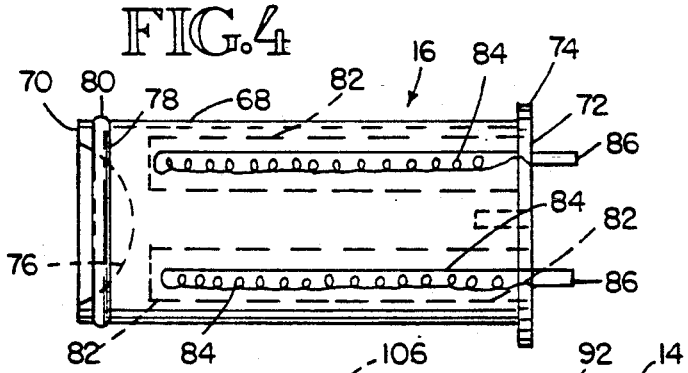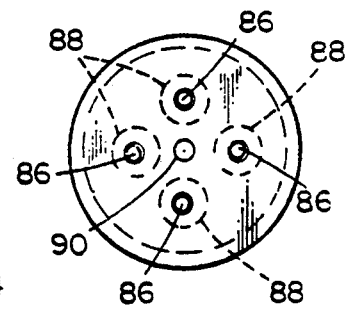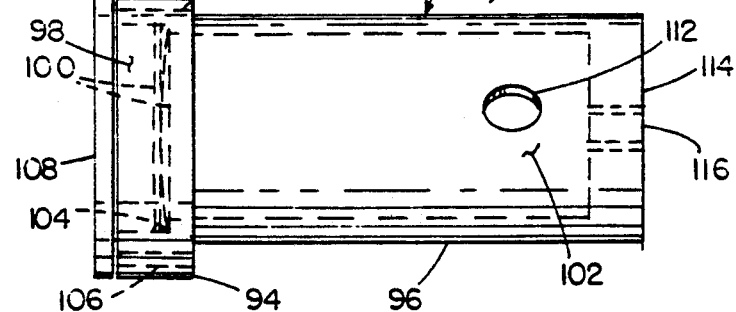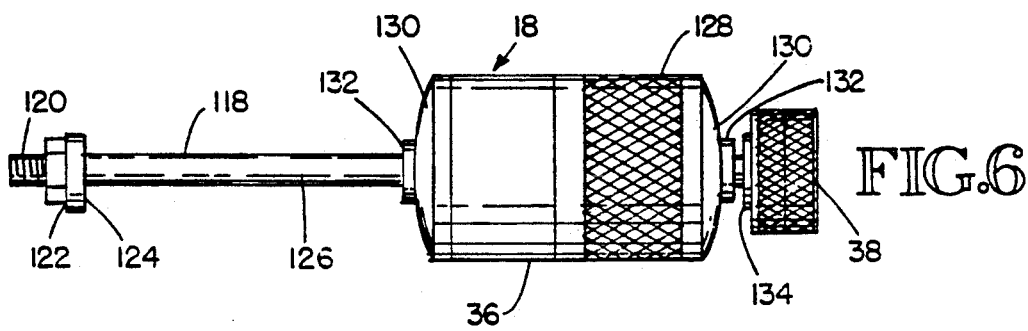

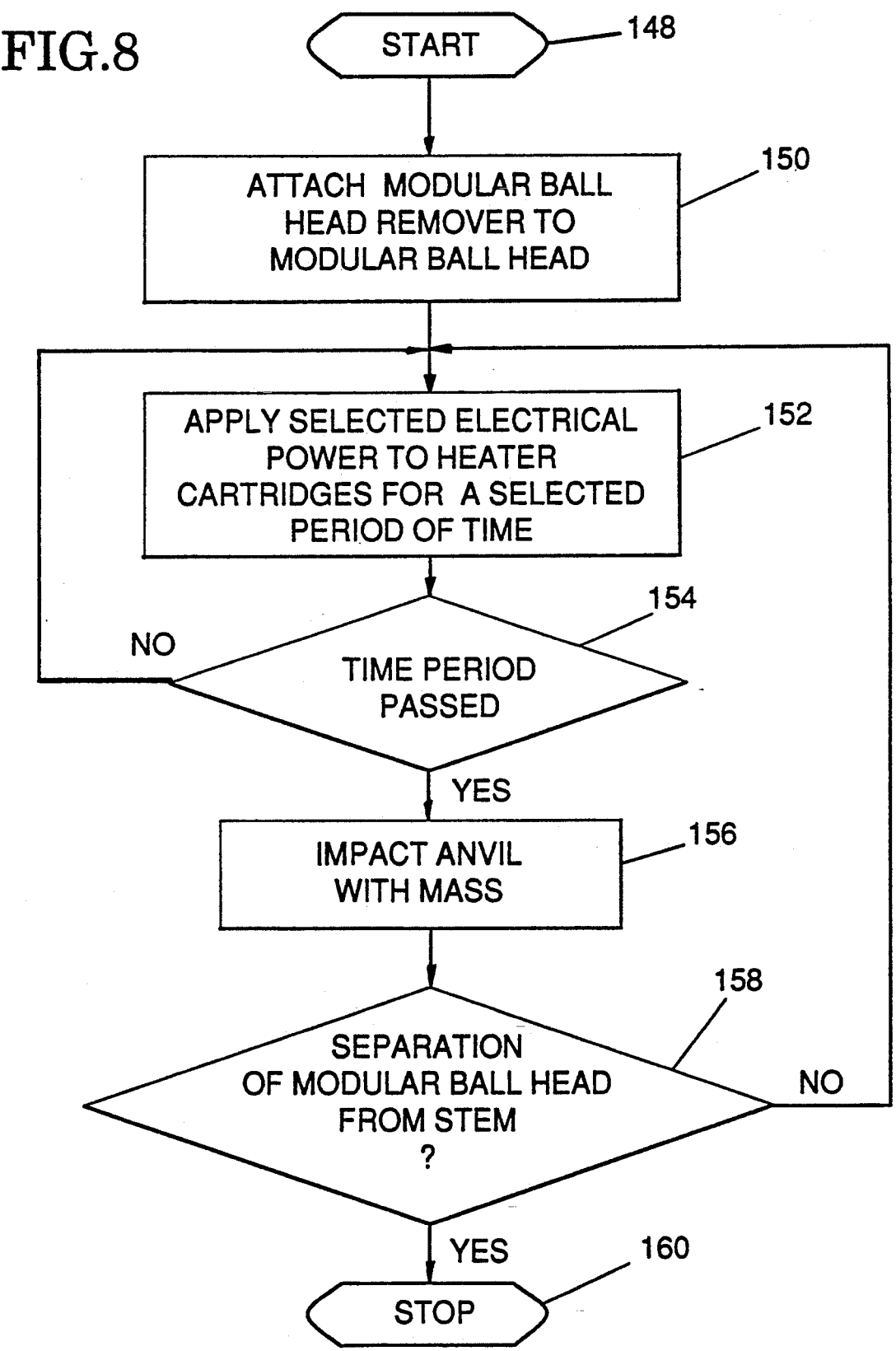

MODULAR BALL HEAD REMOVER

DESCRIPTION

1. Technical Field

The present invention relates to an apparatus and method for removing a modular ball head from a prosthesis stem.

2. Background of the Invention

Because of accident, disease, or other causes, it is frequently necessary to replace a human joint. One common joint replacement is the hip joint. A hip joint replacement involves inserting a prosthesis stem into a femur, cementing or press fitting the prosthesis stem in place, and attaching a hard metal or ceramic ball to a protruding portion of the prosthesis stem. The existing acetabular cup within the hip is then replaced with a polymer polyethylene cup, and the ball head is then placed within the plastic cup.

Hip replacements have proven to be highly successful, providing recipients with improved mobility and reduced pain. One major problem, however, is that after a period of time the ball head may require replacement. Various devices are known which assist removal of the prosthesis stem from the femur. For example, U.S. Pat. No. 3,818,514, to Clark, and U.S. Pat. No. 4,222,382, to Antonsson et al., are typical devices. When using a prosthesis stem with a modular ball head, it is highly desirable to leave the prosthesis stem in place to avoid damage to the femur caused by removal of the sometimes cemented-in-place prosthesis stem. Removal from the femur generally requires great force. The preferred procedure is to replace the ball head while the prosthesis stem remains in place by removing the ball head from the prosthesis stem. Because the ball head can be separable from the prosthesis stem, it is called a modular ball head.

Two opposing requirements exist when attaching a modular ball head to a prosthesis stem. The ball head must remain firmly attached to the stem when in use, but it also must be removable without causing damage to the femur. One approach to meeting both requirements is to provide the prosthesis stem with a tapered ball head retaining shaft and to provide the ball head with a matching tapered opening to receive the shaft. The ball head is mounted by pressing it onto the tapered shaft of the prosthesis stem and impacting it to form a solid connection.

Attaching a modular ball head using a tapered shaft as described above has proven to be a reliable means of attaching the ball head to a prosthesis stem. Frequently, however, the joint between the modular ball head and the tapered shaft of the prosthesis stem becomes so locked together that attempts to remove the modular ball head cause the prosthesis stem to separate from the femur. There is a significant need for an apparatus and method which permits removal of the modular ball head from the tapered shaft of the prosthesis stem, while reducing the likelihood of the prosthesis stem separating from the femur.

SUMMARY OF THE INVENTION

It is an object of the present invention to provide an apparatus and method for removing a modular ball head from a prosthesis stem.

It is another object of the present invention to provide an apparatus and method for removing a modular ball head from a prosthesis stem such that the danger of the prosthesis stem separating from the femur is reduced.

It is yet another object of the present invention to provide medical personnel with an apparatus which reduces the difficulty of separating a modular ball from a prosthesis stem.

The foregoing objects are achieved by the steps of heat expanding the modular ball head and then impacting it in a direction such that it separates from the prosthesis stem. The inventive apparatus which implements the steps includes a heater assembly which produces heat; a housing which attaches to the modular ball head and directs the produced heat to the modular ball head, causing it to expand; and a hammer assembly attached to the housing which provides an impact force which causes the heated modular ball head to separate from the prosthesis stem.

In the preferred embodiment, the housing is thermally insulated to prevent heat from contacting an operator or a patient, and for preventing needless heat loss. The heater assembly includes electrical heater elements powered from a timed, variable output power supply that controls the rate and duration of heat production. The hammer assembly consists of a mass slideably attached to a rod, and which operatively contacts a fixed anvil to create the impact force.

The novel features and advantages of the invention, as well as other objects thereof, will be understood more fully after reading the following detailed description and after reference to the accompanying drawings.

BRIEF DESCRIPTION OF THE DRAWINGS

FIG. 1 is an isometric view of a modular ball head remover according to its preferred embodiment shown next to a prosthesis stem having a modular ball head.

FIG. 2 is an enlarged cross-sectional side view of the remover of FIG. 1 shown with the modular ball head of the prosthesis stem in position for removal.

FIG. 3 is a cross-sectional, side view of the front housing assembly shown in FIG. 1.

FIG. 3A is an end view of the front housing assembly of FIG. 3.

FIG. 4 is a cross-sectional, side view of the heater assembly used with the remover of FIG. 1.

FIG. 4A is an end view of the heating assembly of FIG. 4.

FIG. 5 is a side view of the rear housing assembly shown in FIG. 1.

FIG. 6 is a side view of the hammer assembly shown in FIG. 1.

FIG. 8 is a flow chart of the preferred method of removing a modular ball head from a prosthesis stem.

DETAILED DESCRIPTION OF THE INVENTION

Figure 7:
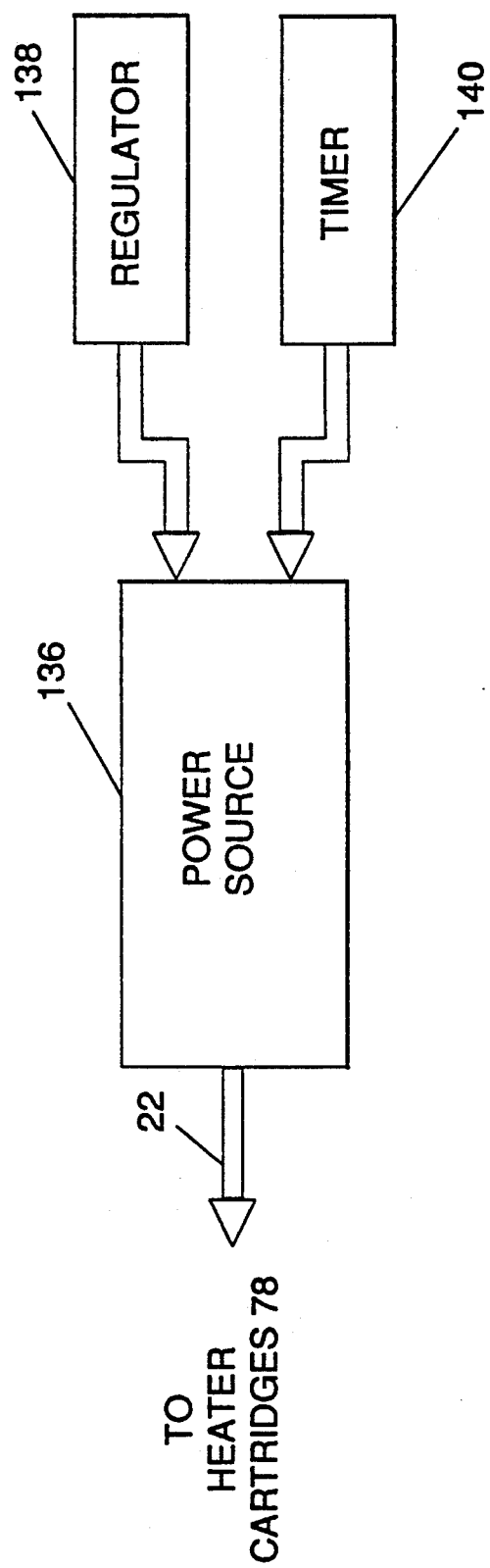
FIG. 7 is a block diagram of the power supply shown in FIG. 1.

As shown in the drawings for purposes of illustration, the invention is embodied in a modular ball head remover 10. The modular ball head remover according to its preferred embodiment is shown in FIG. 1 as including a front housing assembly 12 and a rear housing assembly 14 rigidly attached to the front housing assembly. The front housing assembly 12 encloses most of a heater assembly 16 (shown in FIGS. 2, 4 and 4A), while the remainder of the heater assembly is enclosed within the rear housing assembly 14. A hammer assembly 18 is supported by the rear housing assembly 14. The heater assembly 16 produces heat from electrical energy supplied by a power supply 20 via a power cable 22.

Referring now to FIGS. 2, 3, and 3A, the front housing assembly 12 has an interior cavity 24 with a front opening 26 which receives and captures therein a metal modular ball head 28 on the prosthesis stem 30. The modular ball head 28 has a tapered opening 32 sized to mate with a correspondingly tapered attachment shaft 34 of the prosthesis stem 30 for removably attaching the modular ball head to the prosthesis stem. The heater assembly 16 is thermally coupled to the modular ball head 28. Electrical energy from the power supply 20 causes the heater assembly 16 to heat and expand the modular ball head 28 on the tapered attachment shaft 34. After a selected period of time, long enough to provide sufficient heat to the modular ball head 28 to help loosen it from the tapered attachment shaft 34, an impact force is applied to the modular ball head 28 by the hammer assembly 18.

To generate the impact force, the hammer assembly 18 has an impact mass 36 which is moved by the operator's hand in a quick motion to contact a fixed anvil 38. The resulting impact is transferred to the modular ball head 28, causing it to be removed from the tapered attachment shaft 34 of the prosthesis stem 30, while the prosthesis stem remains fixed in place in a patient's femur. If the initial impact force does not remove the modular ball head 28, one or two additional impacts may be applied. If the modular ball head 28 still does not break free, the heater assembly 16 heats up the modular ball head for a given additional time before the hammer assembly 18 is used again.

The front housing assembly 12 is shown in greater detail in FIGS. 3 and 3A. It consists of a cylinder 40, preferably made of aluminum. The cylinder 40 is encased by a rubber sheath 42 which thermally insulates the cylinder and provides a gripping surface for the operator. The cylinder 40 has an inner bore 44 which extends from end-to-end fully through the cylinder. Positioned coaxially within the bore 44 is a one-piece, cylindrical insulation sleeve 46.

The insulation sleeve 46 is inserted from a front end 48 of the cylinder 40 and has a forward facing, radially extending flange 50 dimensioned to fit flush against a front end wall 52 of the cylinder 40. The interior of the insulation sleeve defines the interior cavity 24 through the front housing assembly 12. When in use, the remover 10 is moved to position the modular ball head 28 within the insulation sleeve 46, entering from the cylinder front end 48, thus placing the insulation sleeve flange 50 toward the patient. The insulation sleeve flange 50 protects the patient from burns when the modular ball head remover 10 is used. The insulation sleeve 46 also thermally insulates the cylinder 40 from the heat produced by the heater assembly 16 and helps retain the heat within the cylinder to more efficiently heat the modular ball head 28. In such manner, heat loss is minimized and burning of the patient and operator is prevented.

Three circumferentially distributed threaded holes 54 are located toward the front end 48 of the cylinder 40 and pass transversely fully through the cylinder sidewall. Threadably received within each of these threaded holes 54 is a thumb screw 56 (only one being shown in FIG. 2). The thumb screws 56 each have a knurled knob 58 which is positioned exterior of the cylinder 40. Corresponding holes are provided in the sheath 42 and the insulation sleeve 46 to permit the thumb screws 56 to pass therethrough.

The threaded holes 54 are located such that when the modular ball head remover 10 is positioned with the modular ball head 28 within the interior cavity 24 of the front housing assembly, the thumb screws 56 can be advanced inward by turning the knurled knobs 58. The knurled knobs 58 are turned until an inner end portion 60 of each contacts the modular ball head 28 near where the tapered attachment shaft 34 of the prosthesis stem 30 enters the tapered opening 32 of the modular ball head 28.

According to the preferred embodiment, the three threaded holes 54 are not located symmetrically around the cylinder 40. It has been found beneficial to form one of the threaded holes 54 at a selected position in the cylinder 40 and then to locate the two other threaded holes 54 at plus and minus 143° from the center of the first threaded hole. This causes two of the threaded holes to be located at approximately 74° from each other. This arrangement eases the difficulty of attaching the remover 10 to a modular ball head 28 when the prosthesis stem 30 is within a femur by minimizing the rotation required of the patient's leg to provide the operator easy access to the thumb screws 56. Essentially, the operator can access one of the thumb screws 56 from one side of the front housing assembly 12 and the other two screws from an opposite side.

The cylinder 40 has a rear end 62 with a rear end wall 64 having four symmetrically located threaded openings 66 therein. These threaded openings 66 receive bolts (shown in FIG. 2) which attach the rear housing assembly 14 to the front housing assembly 12, as will be subsequently described.

As shown in FIGS. 4 and 4A, the heater assembly 16 includes a heater body 68 having a front end 70 and a rear end 72 that terminates in a circular rear plate 74. Milled into the front end 70 is a concavity 76 dimensioned to closely match the contour of the modular ball head 28. A groove 78 is provided near the front end 70 of the heater body 68 to receive an "O" ring 80 that provides a seal between the body and the interior of the insulation sleeve 46 to prevent contaminants from passing therebetween and entering within the rear portion of the front housing assembly 12. The "O" ring also reduces heat loss.

When the heater assembly 16 is inserted within the front housing assembly 12, as shown in FIG. 2, the rear plate 74 engages the rear end wall 64 of the cylinder 40 and prevents the heater assembly 16 from falling through the front housing assembly during use of the remover 10. The length of the heater body 68 is such that when the rear plate 74 contacts the cylinder rear end wall 64, the concavity 76 in the heater body contacts the modular ball head 28 inserted into the front opening 26 of the front housing assembly 12. When the thumb screws 56 are screwed down, the modular ball head 28 tends to be pushed tightly against the concavity 76.

Four circumferentially distributed recesses 82 are provided in the heater body 68 from the rear end 72 thereof and are symmetrically located. These recesses 82 extend partially through the heater body 68 and terminate at a location near the concavity 76. Within each recess 82 is mounted a heater cartridge 84. Each heater cartridge 84 has a heater cable 86 extending rearwardly through a corresponding opening 88 in the rear plate 74. The rear plate 74 is bolted to the heater body 68 using a centrally located threaded bolt 90, as shown in FIGS. 2 and 4A. The heater cables 86 have a smaller radius than the heater cartridges 84. The openings 88 of the rear plate 74 are sized to permit the cables to pass therethrough but retain the heater cartridges 84 in place.

Referring to FIG. 5, the rear housing assembly 14 includes an aluminum shell 92 having a forward flange portion 94 and a cylindrical main body portion 96. The forward flange portion 94 has a diameter larger than the main body portion 96, and almost as large as the diameter of the cylinder 40. The forward flange portion 94 has a cylindrical heater chamber 98 with a diameter slightly greater than that of the rear plate 74 of the heater assembly 16 and with a depth sufficient to hold the rear plate and several spring washers 100 (shown in FIG. 2) therein, as will be subsequently described. Extending rearwardly from the heater chamber 98, but not extending fully through to the rear of the shell 92, is a cable chamber 102. The cable chamber 102 has a smaller diameter than the heater chamber 98, thus defining an annular shoulder 104 at the rear of the heater chamber 98.

The forward flange portion 94 has four circumferentially distributed holes 106 which align with the threaded openings 66 of the cylinder 40. As best shown in FIG. 2, the forward portion of the heater assembly 16 is positioned within the front housing assembly 12 with the rear plate 74 of the heater body 68 engaging the cylinder rear end wall 64. The rearward portion of the heater assembly is positioned within the heater chamber 98 of the rear housing assembly 14. A Teflon washer 108, having openings aligned with the threaded openings 66 of the cylinder 40 and the holes 106 of the forward flange portion 94, is positioned between the rear end wall 64 of the cylinder 40 and the front of the forward flange portion. The two spring washers 100 are positioned between the rear plate 74 of the heater body 68 and the annular shoulder 104 of the rear housing assembly 14. The rear housing assembly 14 is connected to the front housing assembly 12 using four retainer screws 110 (two of which are shown in FIG. 1) which extend through the holes 106 of the forward flange portion 94 and the openings of the Teflon washer 108, and are screwed tightly into the threaded openings 66 of the cylinder 40. This causes the spring washers 100 to be partially compressed against the annular shoulder 104 and thus apply a spring bias on the rear plate 74 of the heater assembly 16 to drive it forward. With the retainer screws 110 tightened, the rear housing assembly 14 is rigidly attached to the front housing assembly 12, and the heater assembly 16 is resiliently secured therewithin in a forwardly biased arrangement.

A cable opening 112 is provided in the sidewall of the main body portion 96 of the shell 92. The four heater cables 86 are positioned together to form the power cable 22. The power cable 22 passes through the cable chamber 102 of the shell 92 and out of the cable opening 112. The power cable 22 is connected to the power supply 20, which supplies electrical energy to the heater cartridges 84.

Referring again to FIG. 5, the shell 92 has a rear end wall 114 with a centrally located threaded opening 116. As best shown in FIG. 6, the hammer assembly 18 is comprised of a rod 118 with a threaded end 120. The threaded end 120 of the rod 118 is threadably received within the opening 116. A lock nut 122 is threadably received on the threaded end 120 to lock the rod in place in the opening. A Teflon bumper 124 is located on the side of the nut 122 away from the shell 92.

Still referring to FIG. 5, the impact mass 36 is slideably disposed on the rod 118. The Teflon bumper 124 provides a cushion when the impact mass 36 is moved forward to the nut 122. The impact mass 36 is a symmetrical, solid, generally cylindrical shaped piece of steel weighing about 12 ounces and having a centrally located axial bore through which a smooth surface portion 126 of the rod 118 passes. The impact mass 36 has an outer surface portion 118 that is knurled to provide a gripping surface for the operator. The impact mass 36 has a tapered portion 130 on each end which terminates in a flat impact surface 132.

The anvil 38 is located on the rearwardmost end of the rod 118, opposite the threaded end 120. The anvil 38 is rigidly attached to the rod 118 and has an impact surface 134 positioned to be engaged by the impact surface 132 at the rearward end of the impact mass 36. In operation, the impact mass 36 is moved rapidly from a starting position adjacent the threaded end 120 towards the anvil 38. Upon contacting the anvil 38, the resulting rearwardly directed impact force is transferred through the rod 118, the rear housing assembly 14, and the thumb screws 56 of the front housing assembly 12 to the modular ball head 28. The impact force tends to cause the modular ball head 28 to separate from the tapered attachment shaft 34 of the prosthesis stem 30.

Referring now to FIG. 7, the power supply 20 includes a power source 136 which is electrically connected to the heater cartridges 84 via the cable 22. The power source 136 supplies electrical power to the heater cartridges 84, causing them to produce heat. The operation of the power source 136 is controlled by a regulator 138 and a timer 140. The regulator 138 limits the electrical power applied to the heater cartridges 84 to the desired rate while the timer 140 controls the amount of time that power is applied to the heater cartridges 84. As shown in FIG. 1, a timer control knob 142 can be adjusted by the operator to select the heating time. The power supply 20 receives power from a wall outlet by way of a power cord (not shown) and a protective fuse 143. An on/off switch 144 is provided to selectively power the power supply 20. The power-on status of the power supply 22 is indicated by an indicator lamp 146 and output power to the heater cartridges 84 is indicated by a timer lamp 147.

According to the preferred embodiment, the power source 136 supplies a regulated output of up to 24 volts at up to 15 amps to the heater cartridges 84. The timer 140 can be adjusted to allow power to be applied for up to 30 minutes. Typically, an application of about 340 watts for about four minutes will expand heat a modular ball head 28 by about 0.00075 inches sufficient so that it can easily be removed from the tapered attachment shaft 34 of the prosthesis stem 30 by using one or two impacts from the hammer assembly 18.

The preferred method of using the remover 10 is illustrated in the flow chart of FIG. 8. Typically, surgery will have been performed to separate the modular ball head 28, prosthesis stem 30, and femur as a unit from the hip joint. The removal process then starts, as indicated by block 188. The initial step is the attachment of the modular ball head remover 10 to the modular ball head 28, as indicated by block 150. This entails placing the front housing assembly 12 over the modular ball head 28 such that the modular ball head contacts the concavity 76 of the heater assembly 16. The thumb screws 56 are then tightened down, causing the front housing assembly 12 to be fully pulled over the modular ball head 28 with the modular ball head forcing the heater assembly 16 backward into the rear housing assembly 14. The spring washers 100 provide a resilient forwardly directed biasing force on the heater body 68 to help achieve and maintain good thermal contact between the modular ball head 28 and the concavity 76.

Next, an operator selects the rate electrical power is to be applied to the heater cartridges 84 and the time period that power is to be applied. Typically, the applied power will be between 250 and 500 Watts and will be applied for three to five minutes. The selected electrical power is then applied for the selected period of time, as indicated by block 152. If the time period has not passed, electrical power continues to be applied to the heater cartridges 84 until such time as the timer times out, block 154. The heater cartridges 84 convert the applied electrical power to heat, which is transferred to the modular ball head 28. After the timer times out, as again indicated by block 154, the impact mass 36 is moved at a rapid rate to contact the impact anvil 38 once or twice, as desired by the operator, as shown by block 156.

Next, a determination is made as to whether the modular ball head 28 has separated from the tapered shaft 34 of the prosthesis stem 30, as indicated by block 158. If the modular ball head 28 has not separated, operation reverts to the steps of block 152. The operator again selects the rate and time electrical power is to be applied. However, if separation has occurred, the operation of the modular ball head remover 10 is complete, as indicated by block 160. Medical personnel may then install a new modular ball head 28 on the tapered shaft 34 of the prosthesis stem 30. The prosthesis stem at all times remains fixed in the patient's femur. The patient is unaffected by the modular ball head removal procedure just described.

From the foregoing, it will be appreciated that, although a specific embodiment of the invention has been described herein for purposes of illustration, various modifications may be made without deviating from the spirit and scope of the invention. Accordingly, the invention is not to be limited except as by the appended claims.

We claim:

1. An apparatus for removing a modular ball head from an attachment shaft of a prostheses stem, comprising:
    a housing receiving the modular ball head therein;
    a member coupling said housing to the modular ball head when positioned therein;
    a heater assembly having a body movably disposed within said housing for movement toward and away from the modular ball head, said heater body including a heat-conductive contact face portion to transmit heat to the modular ball head when positioned within said housing in contact with said heater body face portion, said heater body being biased to move toward the modular ball head and place said heater body face portion in contact with the modular ball head to transmit heat thereto; and
    a hammer connected to said housing to apply an impact force on the modular ball head, said hammer applying said impact force in a direction and with sufficient force to cause removal of the modular ball head from the shaft.

2. The apparatus of claim 1 wherein said heater assembly includes a resistive heating element disposed in and traveling with said heater body within said housing, said resistive heating element generating heat and transmitting the generated heat to said heater body face portion for transmission to the modular ball head.

3. The apparatus of claim 2 further including a power source controlling the heat generated by said resistive heating element.

4. The apparatus of claim 3 wherein said power source includes a timer operatively connected to said resistive heating element, said timer controlling the time during which heat is produced by said resistive heating element.

5. The apparatus of claim 1 further including thermal insulation positioned within said housing between said heater body and said housing.

6. The apparatus of claim 1 wherein said hammer includes:
    a shaft having a front end portion and a rear end portion, said shaft front end portion being connected to the housing;
    an impact anvil having a contact surface and being connected to said shaft rear end portion; and
    a mass slideably mounted on said shaft and selectively movable to contact said impact anvil to apply said impact force to the modular ball head through said housing.

7. The apparatus according to claim 1 further including an insulating sheath external to said housing and providing a gripping surface for said housing, said sheath extending over an end portion of said housing toward the prosthesis stem, whereby the patient who is having the modular ball head removed is protected from burn.

8. The apparatus according to claim 1 wherein said heater body
    face portion has a forward facing concave contact surface having a shape generally corresponding to the surface shaft of the modular ball head to matingly receive the modular ball head therewithin, and
    and said heater body includes a chamber holding a resistive heating element therein.

9. The apparatus according to claim 1 wherein said housing includes a resilient member biasing said heater body toward the modular ball head.

10. The apparatus according to claim 1 wherein said heater body is slideably disposed within said housing between a forward position toward the modular ball head and a rearward position away from the modular ball head, and said housing includes a resilient member biasing said heater body into said forward position.

11. An apparatus for removing a modular ball head from an attachment shaft of a prosthesis stem, comprising:
    an elongated housing having a front portion, a rear portion, and a longitudinal axis, said front portion receiving the modular ball therein;
    coupling members for releasably retaining the modular ball head within said housing front portion;
    a heater assembly disposed within said housing, said heater assembly including:
        a heat conductive body having an elongated chamber and a forward facing, concave end surface engageable with the modular ball head, said body being longitudinally slideable within said housing front portion between a forward position with said concave surface engaged with the modular ball head to transfer heat thereto and a rearward position with said concave surface out of engagement with the modular ball head;

an electrical heating element disposed within said chamber for heating said body; and a resilient member forwardly biasing said body into said forward position with said concave surface engaged with the modular ball head; and a hammer assembly connected to said rear portion of said housing, said hammer assembly including:

an elongated shaft having a front end portion, a rear end portion, and a longitudinal axis, said shaft front end portion being connected to said housing rear portion with said longitudinal axes of said housing and said shaft substantially parallel;

an impact anvil having a contact surface and connected to said shaft rear end portion; and a mass slideably mounted on said shaft and selectively movable to contact said impact anvil to apply said impact force to the modular ball head by said coupling members, the impact force being transmitted via said housing.

12. The apparatus according to claim 11 further including a power source controlling the heat generated by said heating element.

13. The apparatus according to claim 12 wherein said power source includes a timer controlling the time head is generated by said heating element.

14. The apparatus according to claim 11 wherein said housing and said shaft are coaxially aligned.

15. The apparatus according to claim 9 wherein said concave surface has a contour generally corresponding to the surface shape of the modular ball head.

16. The apparatus according to claim 9 further including a thermal insulation sleeve positioned within said housing and about said body to inhibit transfer of heat between said body and said housing.

17. The apparatus according to claim 9 wherein said housing has an exterior sidewall and an annular forward facing endwall, and the apparatus further includes a thermal insulation sheath covering at least a portion of said housing sidewall and forward facing endwall, whereby said sheath prevents burning of the user of the apparatus and the patient on which the apparatus is used.

18. An apparatus for removing a modular ball head from an attachment shaft of a prosthesis stem, comprising:

an elongated cylindrical front housing having a forward end with an opening therein and a rearward end, with an interior chamber axially extending therebetween sized to hold the modular ball head therein, said front housing forward end opening being sized to allow passage of the modular ball head into said front housing chamber;

an elongated cylindrical rear housing having a forward end and a rearward end with an interior chamber extending from said rear housing forward end toward said rearward end, said rear housing having a forward passageway and a rearward passage into said rear housing chamber, said rear housing forward end being attached to said front housing rearward end with said front and rear housing coaxially aligned;

coupling members mounted to said front housing toward said front housing forward end for releasably retaining the modular ball head within said front housing chamber;

a heater assembly disposed within said front housing chamber rearward of said coupling members, said heater assembly including:

a heat conductive body having an interior chamber therein and a forward facing, concave end surface engageable with the modular ball head, said body being longitudinally slideable within said front housing chamber between a forward position with said concave surface engaged with the modular ball head to transfer heat thereto and a rearward position with said concave surface out of engagement with the modular ball head;

an electrical heating element disposed within said body chamber for travel therewith and heating of said body; and at least one wire connected to said heating element for conducting electrical current to said heating element, said wire extending from said heating element into said rear housing chamber through said rear housing forward passageway and out of said rear housing chamber through said rear housing rearward passageway;

a resilient member forwardly biasing said body into said forward position with said concave surface engaged with the modular ball head; and a hammer assembly connected to said rear housing rearward end, said hammer assembly including:

an elongated shaft coaxially arranged with said front and rear housings, and having a front end portion and a rear end portion, said shaft front end portion being connected to said rear housing rearward end;

an impact anvil having a contact surface and connected to said shaft rear end portion; and a mass slidably mounted on said shaft and selectively movable to contact said impact anvil to apply said impact force to the modular ball head by said coupling members, the impact force being transmitted via said rear and forward housings.

19. The apparatus according to claim 18 wherein said front housing rearward end has an opening and said rear housing forward passageway is aligned therewith, and said body has a rearward end portion thereof extending out of said front housing rearward opening and into said rear housing forward passageway, and wherein said resilient member is positioned within said rear housing in engagement with said body rearward end portion.

20. The apparatus according to claim 18 wherein said body chamber extends axially within said body with an open end at a rearward end of said body, and said heating element therein is an elongated resistive heating element extending axially within said body chamber with said wire connected thereto at an end of said heating element positioned toward said body chamber open end.

21. The apparatus according to claim 18 further including a stop member attached to said body to limit forward travel of said body within said front housing chamber.

22. The apparatus according to claim 18 further including a thermal insulating member positioned between said front housing rearward end and said rear housing forward end to inhibit transfer of heat between said front housing and said rear housing.

23. The apparatus according to claim 18, wherein said front housing has a circumferential sidewall, and the apparatus further includes an insulating interior sleeve disposed within said front housing chamber between said circumferential sidewall and said body to inhibit transfer of heat therebetween.

24. The apparatus according to claim 18 wherein said front housing has a circumferential sidewall with a forward facing annular endwall extending about said front housing forward end opening, and the apparatus further includes an insulating exterior sheath covering said circumferential sidewall and said annular endwall, whereby said sheath prevents burning of the user of the apparatus or the patient on which the apparatus is used.

* * * * *

UNITED STATES PATENT AND TRADEMARK OFFICE
CERTIFICATE OF CORRECTION

PATENT NO. : 5,264,680
DATED : November 23, 1993
INVENTOR(S) : Horst R. Seibold and Raymond P. Robinson It is certified that error appears in the above-identified patent and that said Letters Patent is hereby corrected as shown below:

In column 8, claim 8, line 40, please delete "shaft" and substitute therefor --shape--.

In column 9, claim 15, line 33, please delete "9" and substitute therefor --11--.

In column 9, claim 16, line 36, please delete "9" and substitute therefor --11--.

In column 9, claim 17, line 40, please delete "9" and substitute therefor --11--.

Signed and Sealed this

Fifth Day of July, 1994

Attest:

BRUCE LEHMAN

Attesting Officer   Commissioner of Patents and Trademarks